United States Patent [19]

Hagen et al.

[11] 4,279,991

[45] Jul. 21, 1981

[54] PROCESS AND APPARATUS FOR PREPARING MULTI-COMPONENT REAGENT SOLUTIONS

[75] Inventors: Alexander Hagen; Hermann Edelmann, both of Tutzing; Sigmar Klose, Berg, all of Fed. Rep. of Germany

[73] Assignee: Boehringer Mannheim GmbH, Waldhof, Fed. Rep. of Germany

[21] Appl. No.: 100,168

[22] Filed: Dec. 4, 1979

[30] Foreign Application Priority Data

Dec. 7, 1978 [DE] Fed. Rep. of Germany ....... 2852994

[51] Int. Cl.³ .......................... C12Q 1/00; C12M 1/00
[52] U.S. Cl. ........................................... 435/4; 83/71; 83/98; 83/650; 222/309; 222/450; 422/65; 422/100; 435/287; 435/805
[58] Field of Search ................... 435/4, 287, 288, 291, 435/317, 805; 422/65, 66, 100; 222/309, 450, 453; 83/71, 98, 650; 141/83, 104

[56] References Cited

U.S. PATENT DOCUMENTS

| | | | |
|---|---|---|---|
| 3,324,753 | 6/1967 | Lindan | 83/650 X |
| 3,483,780 | 12/1969 | Hudson | 83/98 X |
| 4,085,879 | 4/1978 | Nobuhiro | 83/650 X |
| 4,170,910 | 10/1979 | Stubbings | 83/71 |

Primary Examiner—Robert J. Warden
Attorney, Agent, or Firm—Sprung, Felfe, Horn, Lynch & Kramer

[57] ABSTRACT

The invention provides a process for the production of reagent solutions containing a plurality of components for analytical purposes, wherein the individual components of several differently composed reagents are each introduced into a solid, proportionable carrier material in easily redissolvable form in such an amount that each part by volume or weight of the carrier material carries a definite amount of one reagent component, the carriers of the components are brought together in a magazine-like manner and, for the production of a particular reagent, from all carriers which carry a component of the reagent, there are simultaneously taken off the amounts corresponding to the required amounts of the components, which are then dissolved to form the reagent solution. Apparatus for carrying out the process is also provided.

19 Claims, 6 Drawing Figures

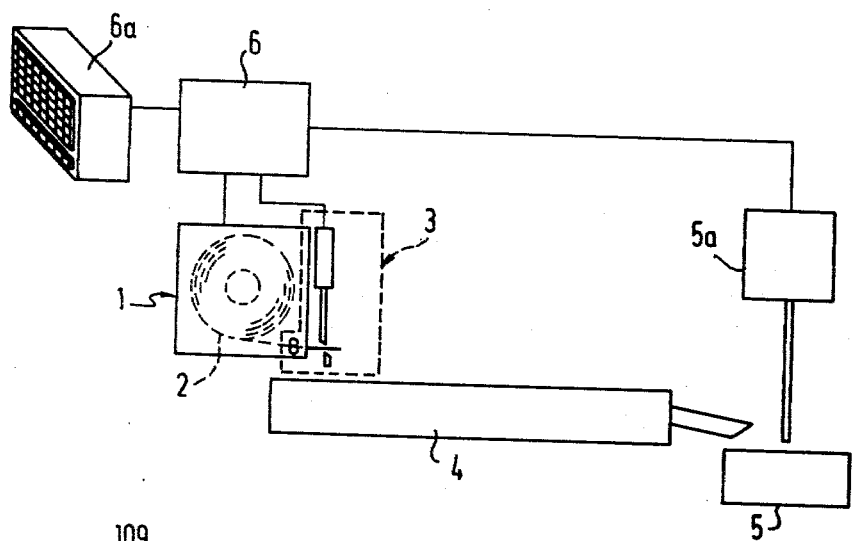
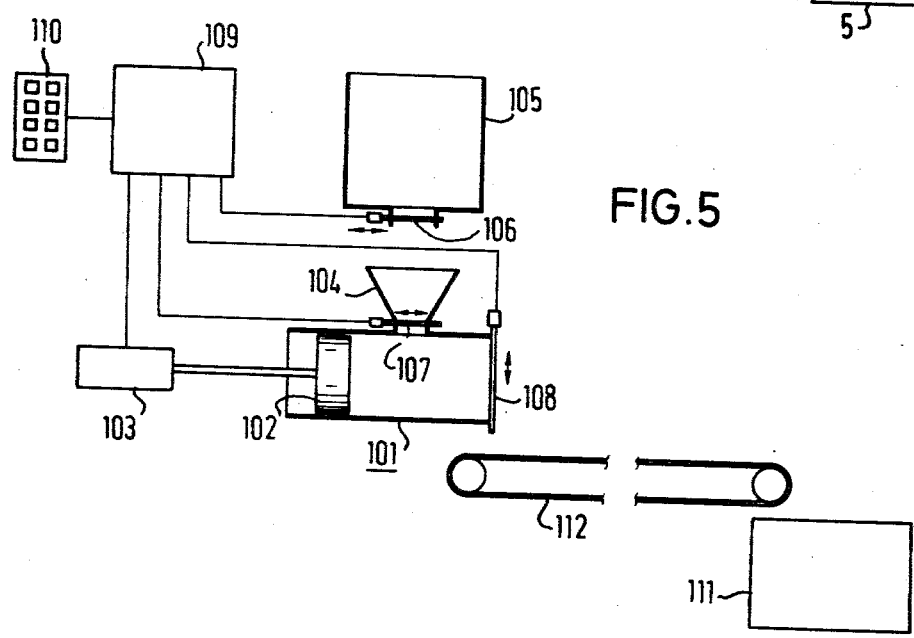

PROCESS AND APPARATUS FOR PREPARING MULTI-COMPONENT REAGENT SOLUTIONS

This invention relates to a process and an apparatus for producing reagent solutions containing a plurality of components.

Reagents, especially those for clinical-chemical analysis usually consist of a plurality of substances, hereinafter referred to as components. In general, the attempt is made to combine as many of these components as possible in a single mixture (solid or as a solution) in order that the user in a simple manual test (for example a photometer test) or in the case of the use of an automatic analyzer has as little work as possible in the preparation of the reagent mixture and, on the other hand, the desired high uniformity of the reagent mixtures can be achieved by the exclusion of possibilites of error in the preparation of the reagent. The aim of combining several components to give a mixture can, however, not be achieved in many cases because, inter alia, incompatibilities of individual materials in the mixture considerably reduce the storage stability.

Therefore, the final reagent solutions are generally prepared by dissolving the substance mixtures or pre-mixtures provided by the producer in a definite manner with water or a buffer and then mixed in a definite manner with a test sample. These solid material mixtures have the disadvantage that they are less stable than the individual components contained therein because, in general, a mutually disadvantageous influencing takes place. On the other hand, these mixtures form a fixed system with definite amount ratios of the individual components which can only be used in a particular and defined manner. In order to be able to used reagent mixtures with differing amount ratios of the individual components, there are to be employed either corresponding, specially prepared mixtures, insofar as these are available commercially, or the reagent mixture is to be prepared ab initio with the use of commercially available raw materials by the user himself. The latter has the disadvantage that, because of varying amounts of impurities in the raw materials, the reagent mixtures can be non-uniform and can display erroneous functions. Only users who are highly qualified and specially trained in chemistry can avoid such errors. Furthermore, it is disadvantageous that this type of reagent production involves a large amount of work for the user.

a further considerable disadvantage in the case of the use of finished solid reaction mixtures depends, in individual cases, upon the accompanying materials added for stabilization. They can, for example, have a negative influence when the nature of the substance to be investigated is variable, for example when using plasma instead of serum for an analysis.

The above-described disadvantages would be eliminated if it were possible to make the solid individual components available in a manner which permits the production of any desired mixtures immediately before carrying out a test.

It would then be possible to produce well-defined mixtures of the individual components and to omit the addition of stabilizing but possibly also interfering adjuvants. Furthermore, the amount ratios could be changed according to need. An endeavor to employ the individual components in such a manner as solid materials is countered by the fact that each test only requires small amounts of these materials and frequently only fractions of a milligram which can only be proportioned with great difficulty. In particular, however, it would appear to be a practically insoluble problem to weigh out from a plurality of, in all, at least 50 different solid materials with differing properties (fluidity, hygroscopic properties and the like) so quickly the necessary small amounts and convey then to the place at which the analysis is to be carried out that, in this way, there is possibly a test principle which is adequate for the present state of the art. It is to be borne in mind that, in commercially available automatic devices (for example the SMAC system of the firm Technicon), about 2000 individual tests per hour are made. If the individual components per test are to be obtained by weighing out from storage vessels, then about 10,000 weighings per hour would have to be made, it thereby being assumed that, on average, five different individual components are necessary per mixture. Consequently, more than 2 weighings of high precision in the mg. range would have to be carried out per second which, with the means at present known and available, can be regarded as being something without any prospect of success.

The substances would be measurable if they were present in the form of solutions, i.e. were not used as solid materials. Then, however, the stabilities would frequently be insufficient.

Therefore, the problem forming the basis of the present invention is to overcome the above-described disadvantages and to provide a process and a device which permit the production of reagent mixtures of the described type immediately before the test.

Thus, according to the present invention, there is provided a process for the production of reagent solutions containing a plurality of components for analytical purposes, wherein the individual components of several differently composed reagents are each introduced in a solid, proportionable carrier material in easily redissolvable form in such an amount that each part by volume or weight of the carrier material carries a definite amount of one reagent component, the carriers of the components are brought together in a magazine-like manner and, for the production of a particular reagent, from all carriers which carry a component of the reagent, there are simultaneously taken off the amounts corresponding to the required amounts of the components, which are introduced into a reagent solvent, in order to dissolve the components.

The principle forming the basis of the process according to the present invention is to absorb the individual solid components of reagents on solid carrier materials and to dissolve these immediately before commencement of the test. Since, according to the present invention, they are present in unit amounts per carrier unit, for the purpose of proportioning they no longer need to be weighed out but can simply be counted.

As individual components within the scope of the present invention, ther come into consideration all components of reagent solutions which can be introduced on to a solid carrier material in storage-stable form in such a manner that they can be rapidly dissolved by conventional carrier solutions for reagents. The reagent solvents to be used according to the present invention are mainly aqueous solvents. Typical examples for individual components include enzymes, co-enzymes, substrates, salts, buffer substances, indicator substances, surface-active materials and adjuvants. All these individual components are known to the art skilled and do not need to be explained here in more detail. The individual components can possibly be present on a carrier together with stabilizing agents.

The carrier materials which can be taken into consideration are mainly absorbent substances in strip or particulate form, paper being especially suitable. Examples of other carrier materials which can be used include foils, such as metal foils, porous plastic films, particles with absorbent surface layers and the like. Strip-like carrier materials, from which the required amounts can be cut off or punched out, are especially preferred because of their simple proportionability. However, solid particles can also be used, especially when they are relatively small in comparison with the minimum amount necessary which, in the scope of the reagents coming into consideration, are needed of a particular component. In this case, the amounts can be counted out or measured volumetrically. Such solid particles have the advantage that they can have a non-absorbent core which has a relatively high specific weight so that the transport of the measured out amount of carrier material can be achieved, without special means, solely by gravity with the desired speed.

The individual reagent components can be applied to the carrier materials by all methods which ensure a rapid redissolving. Particularly preferred is the application of solutions of the reagent components, for example by dropping on or dipping in, with subsequent removal of the solvent. However, the application can also be carried out by means of readily soluble binding agents, adhesives or the like. Furthermore, it is also possible to microencapsulate the individual components in a readily soluble encapsulation material and then either to bond the microcapsules together with the formation of the carrier structure or to fix them on to the actual carrier, for example, by adhesion, introduction into a paper structure or the like. The methods to be used for this purpose are also well known from other fields of technology, for example in the field of data transmission and in the production of papers suitable for this purpose.

By a magazine-like combination of the carriers, it is to be understood that these are so arranged in close spatial relationship to one another than the amounts of carriers necessary for the production of a particular reagent solution, which can be the same or different from one carrier to another, can be cut off and transported into the reagent solvent practically simultaneously. A magazine-like spatial combination of the carriers can take place within a common housing; alternatively, the combination can take place also on a common holding means. It is only necessary that each individual carrier material for a reagent component can be proportionated independently of each other, but can be cut off and transported simultaneously therewith, which are necessary for the same reagent.

"Simultaneously" means, according to the present invention, that the take off of the individual carrier materials is to take place within a finite period of time which is small in comparison with the total time available for the production of the reagent solution. If the process is to be employed in conjunction with automatic analysis apparatus in which, for example, every 10 seconds a reagent solution has to be made available, then, in this case, a period of time of about 1 to 2 seconds is to be regarded as being small.

The carrier material for the reagent components must consist of a material which is inert with regard to the reagent solution and to the measurement to be carried out therein and which can possibly be easily removed mechanically from the solution, for example by centrifuging, filtering or the like.

By means of the carrier material, it is possible to make available the individually much too small amounts of the reaction components in a readily proportionable form. Therefore, according to the present invention, the carrier serves as a "dilution means" for the reagent components. Furthermore, it frequently brings about a stabilization. In addition, the carrier makes it possible to convert per se non-fluid substances, for example liquid or sticky components, into easily handled and proportionable compositions.

The present invention also provides a device for the production of reagent solutions for analytical purposes which contain a plurality of components, comprising a magazine, which contains a plurality of carrier materials, each of which carries, per unit weight or volume, a definite amount of an individual component of a reagent, a proportioning device which, from several carrier materials, enables definite amounts to be measured off and separated off, preferably simultaneously, a conveyor device for transporting the amounts of carrier separated off to a solvent container and a control device which controls the proportioning device for each desired reagent composition.

For a better understanding of the present invention, reference will be made to the accompanying drawings, in which:

FIG. 1 is a schematic illustration of a device according to the present invention;

FIG. 5 is a schematic view of another embodiment of a device according to the present invention.

Figure 2:
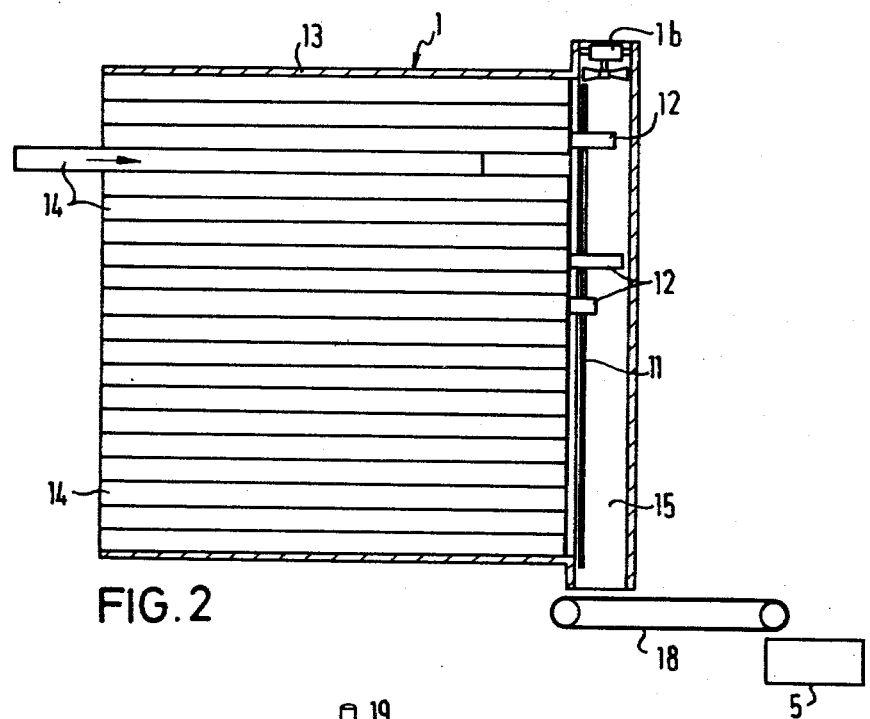
FIG. 2 is a vertical section through a magazine with carrier materials.

In FIG. 1, there is schematically illustrated a device according to the present invention for the production of reagent solutions for analytical purposes. A magazine (1) contains carrier materials (2) in the form of paper rolls, the ends of which protrude from the magazine and a definite length of which can be measured off and cut off by a proportioning device (3). The paper strips cut off drop on to a conveyor device (4) which transports them to a solvent container (5), where the individual components are dissolved to give the desired final reagent solution. The control device (6), which itself is controlled by a selector device (6a), controls the proportioning device (3) in such a manner that, for each desired reagent composition, the required amounts of carrier materials are measured off and separated off; furthermore, it controls a reservoir (5a), which provides solvent to the solvent container (5).

Figure 3:
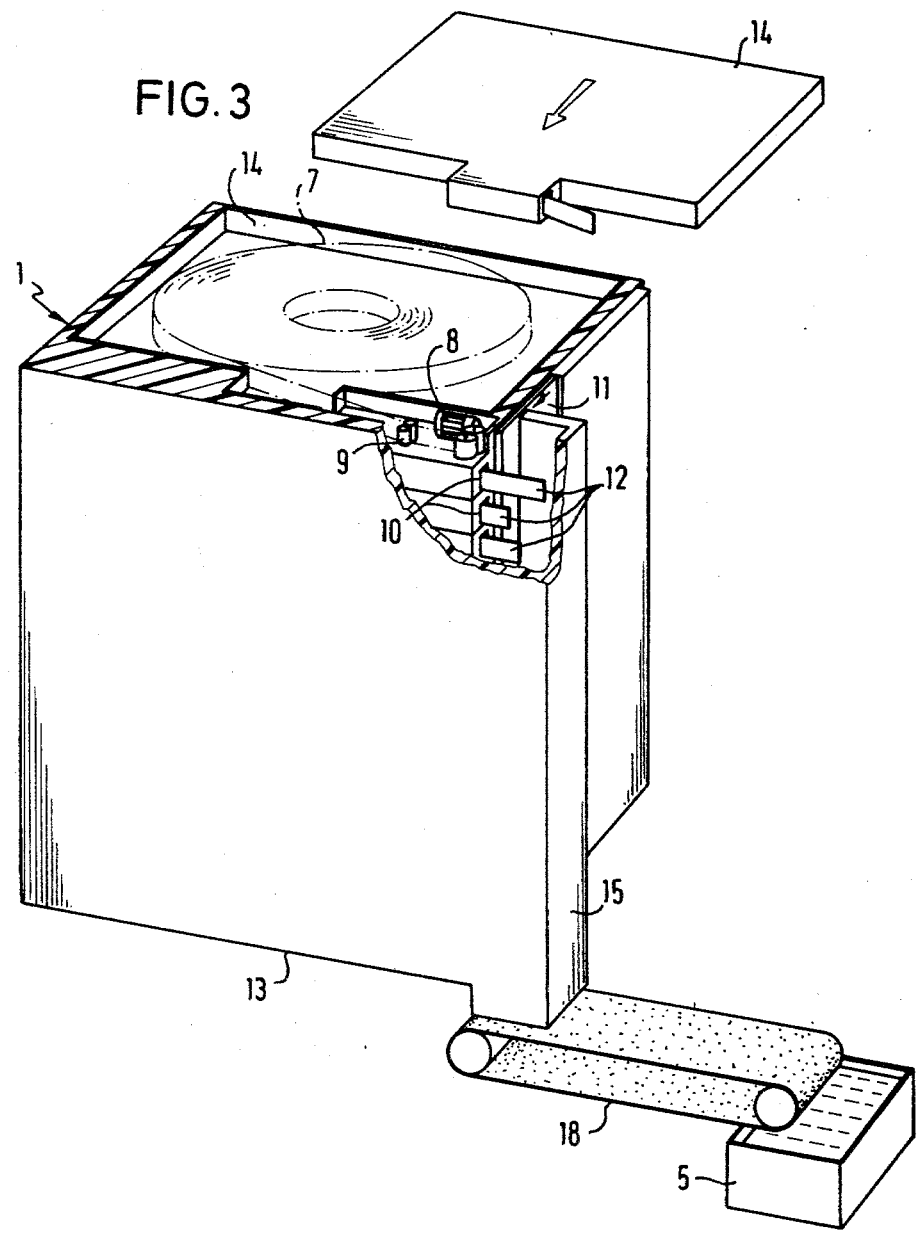
FIG. 3 is a perspective and partially sectional view of the magazine of FIG. 2.

FIGS. 2 and 3 illustrate one embodiment of the magazine (1) and of the proportioning device in more detail. The magazine (1) contains, in a magazine housing (13), a plurality of carrier materials, arranged side-by-side, in the form of paper strip rolls (7), each of which is in a cassette (14). If necessary, the cassettes (14) can be individually removed from the magazine (1) and replaced. For each cassette (14), the magazine (1) has an opening (10), from which, by means of the proportioning device, a definite length of paper can be pushed out and cut off. The proportioning device (3) thereby has, per paper strip roll (7), a stepping motor (8), controlled by the control device (6), which motor operates a push-forward device in the form of a pair of rollers (9) optionally provided with transport teeth. By means of the roller pair (9), the length of paper strip necessary for the particularly needed amount of a reagent component is thereby pushed out of the appropriate magazine opening (10); by means of a cutting device (11), associated with the proportioning device, which comprises, for example, a knife arranged parallel to the magazine openings (10), the emergent strip sections (12) are cut off practically simultaneously.

The magazine openings (10) lead into a wind tunnel (15) attached to the magazine housing (13), which tunnel has a blower (16); this draws in air from above and forces it downwardly through the wind tunnel. On the lower end of the wind tunnel (15), there is arranged a sieve-like conveyor band (18) which provides the connection to the solvent container (5). The windtunnel (15), the blower (16) and the conveyor band (18) together form the conveyor device (4), which introduces the pieces of paper strip into the solvent in the solvent container (5). In the case of this embodiment, the wind tunnel (15) is connected with the magazine housing (13) in such a manner that the magazine openings (10) are present on the wall of the wind tunnel.

Figure 4:
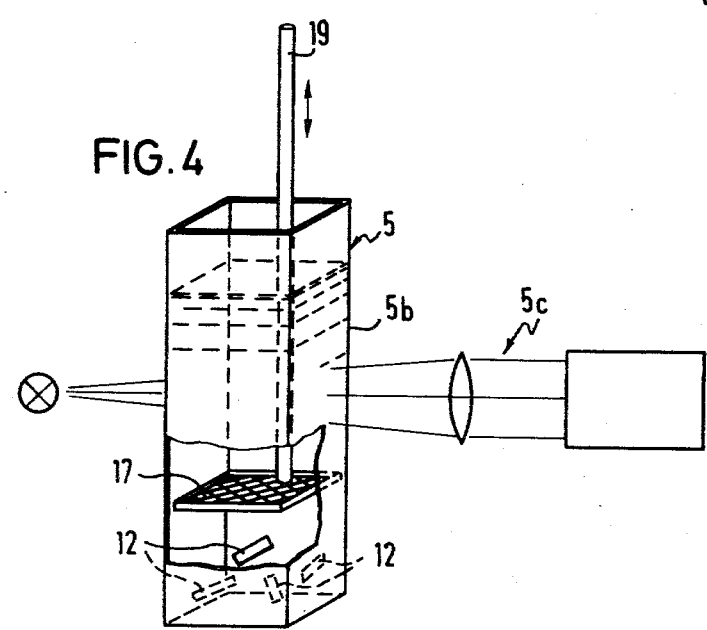
FIG. 4 is a perspective view of one embodiment of a solvent container.

FIG. 4 illustrates one embodiment of the solvent container (5). It comprises a cuvette (5b), the side walls of which consist of an optically clear material, such as quartz glass, a synthetic resin or the like, and are, therefore, suitable for use for direct optical measurements in the solution. The cuvette (5b) can be placed in a corresponding cuvette container of a measuring device, for example of a photometer, especially when the reagent solution produced is used for carrying out individual determinations, such as are frequently used in a physician's laboratory. However, the cuvette (5b) can also be part of an automatic analysis device and can be arranged in such a manner that, after the addition of the sample to be investigated, direct optical measurements are carried out, without the cuvette (5b) having to be further transported for this purpose. In order to have the desired clarity for optical measurements, there is provided a rod-like holding means (19), the height of which is adjustable and the lower end of which carries a sieve-like plunger (17) aligned with the cuvette (5b). This plunger (17) moves, after introduction of the pieces of paper strip (12), downwardly in the cuvette (5b) and is so adapted thereto that the pieces of paper strip cannot pass around its outer edge. This downward movement of the plunger (17) removes the pieces of paper strip from the path of light so that they cannot disturb the optical measurement. The downward movement of the plunger also ensures simultaneous mixing of the reagent and sample.

The measurement device of the automatic analyzer is indicated generally with (5c).

The control device (6) can be constructed in any desired manner. It is important that it makes possible, for each desired reagent composition, the appropriate measurement of the required individual components. For this purpose, it preferably comprises an electronic device which controls the proportioning and separating off device (3) in such a manner that the particularly required amounts of the individual carriers are made available. In the case of the embodiment illustrated in FIG. 3, for this purpose the individual stepping motors (8) are merely operated until the strip sections (12) have been pushed out for the desired length. Subsequently, they are cut off.

Instead of the cutting device (11), it is, for example, also possible to provide a punch which is so adapted that, from the carrier strip, it can cut out a large but selectable number of pieces of equal size. Such punches are known. They are used, for example, in telex apparatus for the production of punched tapes. Such devices are able to cut out from a strip up to 250 pieces per second or to cut off such pieces when the strip has only been coated or impregnated in a punctate manner. Due to the high large number of pieces which can be produced per second, there are obtained very small unit amounts of particular reagent components so that the composition of the reagent solutions can be varied with extremely small gradations.

If the carrier material consists of solid particles, for example of power, granulate, spheroids or the like, then measurement devices based on volume or weight can be used. Appropriate measurement devices based upon volume measurement make use of measuring chambers of adjustable size.

FIG. 5 illustrates an embodiment with a measurement chamber (101) of variable volume, the volume of which can be altered by a piston (102) on a linear motor (103). The measurement chamber (101) receives the blendable solid carrier material through a funnel (104) from a supply container (105). On the outlet of the supply container (105) there is a first slide valve (106), on the inlet of the measurement chamber (101) there is a second slide valve (107) and on the outlet of the measurement chamber there is a third slide valve (108). The piston (102) can, in addition to the volume determination, also push out the carrier material from the measurement chamber (101). The moving parts are controlled from a control device (109), which is provided with a selector device (110). The carrier material passes from the measurement chamber (101) to a conveyor device (112), which conveys the material to a solvent container (111). Similarly to the previously described embodiment, several measurement chambers can be associated with the conveyor band (112).

The control device, for example an electronic control, must control at least the forward movement of the conveyor band or the amount of carrier material which is to be taken from each part of the magazine. In addition, it can also operate the cutting device and regulate the amount of solvent which is introduced into the solvent container (5), the speed of transport, when mechanical transport means are used for conveying the measured amounts of carrier to the solvent, and the like. However, these functions are not absolutely essential.

The input into the electronic control can take place according to all methods usual for the control of such devices, for example by means of keys, punched tapes, coding cards and the like. All these possibilities are known and do not need to be described here in detail.

Within the scope of the present invention, it is preferred to use an aqueous solvent to which all the components of the reagent are added only later. However, it is also possible to use a buffer as solvent, although this impairs the variability of the reagent solutions to be prepared. However, for certain fields of use, this disadvantage is acceptable.

The dissolving off of the reagent components from the carrier in the reagent solvent, i.e. usually water, can be promoted by movement. This movement can be provided for by stirring, shaking, vibrating or the like.

By means of the present invention, it is possible to use the individual reaction components in many different reagents, depending upon how they are needed, without hereby being bound to the other components simultaneously needed in a particular reagent. In this way, it is also possible to employ reaction components in test reagents which, because of their unsatisfactory storage stability in the presence of other components, cannot be used for normal reagent combinations since they do not have the required storage stability. Simultaneously, however, the requirements for the stability of the individual components are reduced since there is now no longer a danger that components of less frequently used reagents have to be stored in a mixture for months on end. Another important factor is that the carrier, which serves as a "dilution means", can also bring about a stabilization of the individual components. Furthermore, in this manner, it is possible to use nonfluid substances in an easily proportionable form.

Furthermore, according to the present invention, the dependability of production is increased since the individual reaction components are, in each case, only produced in a very simple system which, as a rule, merely consists of a single chemical compound, i.e. the reagent component, and the carrier and thus sources of error due to the simultaneous presence of other components are excluded. In the case of premixed reagents of a plurality of components, an error, for example a proportioning error in the case of a single component, could make a whole production batch useless. Another important advantage is the great flexibility of the process according to the present ivention. The present invention makes possible a combination of an extremely simple handling of pre-mixed reagent combinations with the advantage of the storage stability of the individual reagents which, in many different reagent combinations, mostly represent a single component. With a relatively limited number of individual components, for example about 50, it is possible to produce an extraordinarily large number of differently composed reagents with extraordinary speed and according to need. Hitherto, however, it was necessary to keep a supply of each of the many different reagent combinations for the various test processes.

The advantages provided by the present invention can be utilized not only in large automatic analyzers but also in a simple physician's laboratory. In the case of automatic devices, as a rule, the capacity thereof is increased since the various reagent solutions can be made available much more quickly. Within the course of a few seconds, it is possible to feed greatly differing reagents into the automatic system. In the case of this embodiment of the present invention, the device according to the present invention can be directly integrated with an automatic analyzer so that, for example, the solvent container is simultaneously a part of the automatic system, supplying solvent and sample in a predetermined rhythm.

The following Examples are given for the purpose of illustrating the present invention; in these Examples, the following abbreviations are used:

GOT: glutamate-oxalacetate transaminase
GPT: glutamate-pyruvate-transaminase
LDH: lactate dehydrogenase
α-HBDH: α-hydroxybutyrate dehydrogenase
NADH: reduced nicotinamide-adenine-dinucleotide
MDH: malate dehydrogenase

EXAMPLES

For the determination of the enzymes GOT, GPT, LDH and α-HBDH, all of which are of clinical-chemical importance, four different reagent combinations are necessary which, in all, contain nine different individual components but in differing amounts. In the following Table I, there are set out the nine individual components and the amounts thereof necessary in each of the reagents, in each case referred to a solution volume of 1 ml.:

TABLE I

| No. | component | GOT | GPT | LDH | α-HBDH |
|---|---|---|---|---|---|
| 1 | phosphate buffer | 80 μmol | 80 μmol | 50 μmol | 50 μmol |
| 2 | NADH | 0.18 μmol | 0.18 μmol | 0.18 μmol | 0.18 μmol |
| 3 | MDH | 0.6 U | — | — | — |
| 4 | LDH | 1.2 U | 1.2 U | — | — |
| 5 | α-ketoglutarate | 12 μmol | 18 μmol | — | — |
| 6 | L-aspartate | 200 μmol | — | — | — |
| 7 | L-alanine | — | 800 μmol | — | — |
| 8 | pyruvate | — | — | 0.6 μmol | — |
| 9 | α-ketobutyrate | — | — | — | 3 μmol |

If solutions of these components are applied to strips of filter paper and dried so that each unit surface area of the paper contains a definite amount of adsorbed component, then, by simply cutting off an appropriately sized piece of paper strip and introducing it into water, each of the four reagent compositions can be produced in an extremely short period of time.

If the same components are applied to particulate carriers, then it is necessary that each individual component is present in a unit amount per particle or volume of particles, a plurality of which gives exactly and precisely the amount needed for each reagent. Such unit amounts and the pluralities thereof needed for the individual reagents are shown in the following Table II.

TABLE II

| No. | component | GOT | GPT | LDH | α-HBDH |
|---|---|---|---|---|---|
| 1 | phosphate buffer | 8 (10 μmol) | 8 | 5 | 5 |
| 2 | NADH | 1 (0.18 μmol) | 1 | 1 | 1 |
| 3 | MDH | 1 (0.6 U) | — | — | — |
| 4 | LDH | 1 (1.2 U) | 1 | — | — |
| 5 | α-ketoglutarate | 2 (6 μmol) | 3 | — | — |
| 6 | L-aspartate | 1 (200 μmol) | — | — | — |
| 7 | L-alanine | — | 1 (800 μmol) | — | — |
| 8 | pyruvate | — | — | 1 (0.6 μmol) | — |
| 9 | α-ketobutyrate | — | — | — | 1 (3 μmol) |

As carriers for such unit amounts, there can be used, for example, particles of synthetic resins, noble metals, stainless steel, porous glass, porous ceramic and the like.

For the production according to the present invention of the above four reagents, with the use of the device illustrated in FIGS. 1 to 3 of the accompanying drawings, in the magazine (1) are placed nine cassettes (14), each of which contains a paper roll containing the components set out in Table I. For the production of the GOT reagent, an appropriate punched card is inserted into the control device (6). The control device controls the proportioning device (3) in such a manner that, from the magazines which contain the paper strips with components 1 to 6 of Table I, a length of the paper strip corresponding to the particular required amount of substance is punched out into the wind tunnel (15) and thereafter together with the other strips simultaneously is cut off. The pieces of cut off paper are blown by the current of air produced by the blower (16) into the solvent vessel (5) where, within the course of 1 to 2 seconds, the individual reagents are dissolved off from the carrier to give the final reagent solution.

The three other reagent solutions are produced in a corresponding manner.

In the following, as a further Example, there is described an embodiment of the cassette and of the paper strip which permits an especially simple introduction into the magazine because the transport of the beginning of the strip can be carried out automatically in the cutting device in such a manner that even the first newly cut off piece of paper gives the correct amount proportionating.

In order to achieve these advantages, the strip is printed over its whole length with a striated incremental measure, the printing color being so chosen that it does not give rise to any chemical side effects. Instead of this, use can also be made of a double row of perforation holes staggered with regard to each other in the direction of the length of the strip and a toothed wheel engaging same to push the strip forward.

The magazine has a transport stop which is first released by the insertion of the cassette into the magazine. With the help thereof, the start of the paper strip, after being exactly cut after production, can be fixed at a definite and protected point within the cassette. With the help of an optical senser unit in the magazine, by means of the electronic control, after insertion of the cassette, such a fixed length of strip is transported from the cassette that the start of the strip is exactly on the cutting device.

After the readiness of the magazine has thus been produced again, the sensing of the printed incremental measure serves, from now on, for the proportioning. The minimum unit amount is thereby not limited by the raster of the measure since several sensors can be employed which are arranged in such a manner that, relatively to the cassette and thus also to the cutting device, smaller steps can also be made. The cassette is thereby fixed in the magazine by appropriate guides at a definite and reproducible point.

An important advantage of this embodiment, with the use of an incremental measure, is that even a slight slip of the transport wheel cannot give rise to a proportioning error.

The incremental control also makes it possible to recognize the end of the strip, to stop the magazine and, indicating which cassette it is, indicates the need for its replacement.

Figure 6:
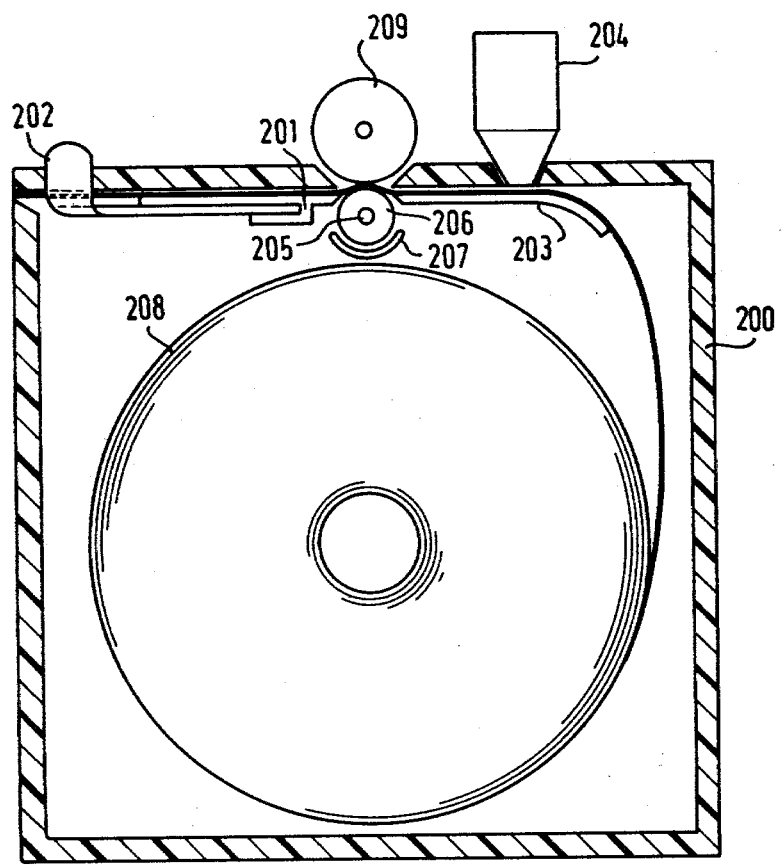
FIG. 6 is a sectional view of another embodiment of a magazine with carrier material.

A cassette which can be used for this embodiment is shown in FIG. 6 of the accompanying drawings.

A cassette (200), which can be produced by injection moulding, has a holding means (201) for an elastically prestressed transport stop (202), a band guide (203) behind an optical sensor (204) and an axle pin (205) for a pressure wheel (206), as well as a covering therefor (207) against the paper band roll (208), which can be incorporated in the injection moulding tool. The sensor unit (204) and an elastically pressed on transport wheel (209) are fixed in the axtual magazine housing. The pressure wheel can also be omitted; the band guide and the holding means of the transport stop then pass directly from one to the other.

It will be understood that the specification and examples are illustrative, but not limitative of the present invention and that other embodiments within the spirit and scope of the invention will suggest themselves to those skilled in the art.

What is claimed is:

1. A process for the preparation of a multi-component reagent solution, comprising:
   providing each of a plurality of individual reagent components in a redissolvable form on a separate solid carrier capable of being formed into discrete sub-elements carrying a defined amount of a reagent component of said plurality of reagent components; simultaneously forming sub-elements from at least one solid carrier; and introducing the sub-elements into a common reagent solvent to dissolve the associated reagent components and form the reagent solution.

2. A process as claimed in claim 1 wherein said carrier comprises paper or film the required amount of which is cut off or punched out.

3. A process as claimed in claim 1 wherein the carrier is particular material with an absorbent surface layer and the required amounts being measured volumetrically or by counting.

4. A process as claimed in claim 1 wherein said individual components are selected from enzymes, coenzymes, substrates, salts, buffer substrates, indicator substances, surface-active substances and adjuvants.

5. A process as claimed in claim 1 wherein said components are introduced into said carrier by applying a solution of the component to the carrier and then drying same.

6. A process as claimed in claim 5 wherein the components are dissolved in an organic solvent.

7. A process as claimed in claim 1 wherein said reagent solvent is water.

8. Apparatus for the preparation of reagent solutions for analytical purposes containing a plurality of individual components which apparatus comprises a magazine containing a plurality of carrier materials each of which carries, per unit volume or weight, a defined amount of an individual reagent component, a proportioning device capable of measuring and separating off defined amounts from several carrier materials, conveyor means for transporting the separated-off amounts of carrier to a solvent container, and control means which actuates and controls said proportioning device for any specific reagent composition.

9. Apparatus as claimed in claim 8 wherein said proportioning device is capable of measuring and separating off defined amounts of carrier materials from more than one carrier material.

10. Apparatus as claimed in claim 8 wherein said carrier materials are in the form of a roll of paper strip, said magazine includes openings for outputting the strips and said proportioning device comprises paper advancing means, controlled by the control device, adapted to advance defined lengths of the paper strip through the magazine openings, and a cutting device for each advancing means for cutting off lengths of strip emerging from the magazine openings.

11. Apparatus as claimed in claim 10 wherein said magazine comprises a housing and cassettes insertably arranged therein, each cassette containing a carrier strip.

12. Apparatus as claimed in claim 10 wherein said cutting device is capable of cutting off simultaneously lengths of several strips emerging from said magazine openings.

13. Apparatus as claimed in claim 10 wherein the conveyor means includes a conveyor device comprising a conveyor band adapted to transport separated carrier materials to the solvent container.

14. Apparatus as claimed in claim 13 wherein said conveyor means further comprises a wind tunnel and a blower.

15. Apparatus as claimed in claim 14 wherein said wind tunnel is connected with the magazine housing in a manner that the magazine openings are operatively connected to the wind tunnel.

16. Apparatus as claimed in claim 10 wherein said push-forward device comprises a toothed wheel which engages a corresponding perforation in the carrier strip.

17. Apparatus as claimed in claim 10 wherein the proportioning device comprises a punch which is adapted to cut out from the carrier strip a predetermined number of pieces of equal size.

18. Apparatus as claimed in claim 10 wherein the solvent container comprises a cuvette made of an optically clear material.

19. Apparatus as claimed in claim 18 wherein said cuvette contains a rod-shaped member of adjustable height the lower end of which carries a sieve-like plunger.

* * * * *

UNITED STATES PATENT AND TRADEMARK OFFICE
CERTIFICATE OF CORRECTION

PATENT NO. : 4,279,991

DATED : July 21, 1981

INVENTOR(S) : Alexander Hagen et al.

It is certified that error appears in the above—identified patent and that said Letters Patent is hereby corrected as shown below:

Cover page, the address of the Assignee should be

Boehringer Mannheim GmbH
Mannheim-Waldhof, Fed. Rep. of Germany

Signed and Sealed this

Twenty-third Day of February 1982

[SEAL]

Attest:

GERALD J. MOSSINGHOFF

Attesting Officer     Commissioner of Patents and Trademarks